United States Patent [19]

Crone, Jr. et al.

[11] 4,314,091
[45] Feb. 2, 1982

[54] PREPARATION OF 1-METHYL-3,5-DIISOPROPYL BENZENE FROM CHARGE STREAMS CONTAINING DIISOPROPYL TOLUENE

[75] Inventors: John M. Crone, Jr., Fishkill; Robert M. Suggitt, Wappingers Falls, both of N.Y.

[73] Assignee: Texaco Inc., White Plains, N.Y.

[21] Appl. No.: 135,609

[22] Filed: Mar. 31, 1980

[51] Int. Cl.³ .............................................. C07C 4/12
[52] U.S. Cl. .................................... 585/486; 585/474; 585/477; 585/480; 585/483
[58] Field of Search ............... 585/474, 477, 480, 483, 585/486

[56] References Cited
U.S. PATENT DOCUMENTS

| | | | |
|---|---|---|---|
| 2,385,524 | 9/1945 | Mattox | 585/474 |
| 2,648,713 | 8/1953 | Schneider | 585/486 |
| 2,734,929 | 2/1956 | Doumani | 585/433 |
| 2,744,150 | 5/1956 | Enos | 585/474 |
| 2,795,630 | 6/1957 | Lien et al. | 585/474 |
| 2,963,518 | 12/1960 | Amos et al. | 585/445 |
| 3,555,103 | 1/1971 | Strohmeyer | 585/474 |

*Primary Examiner*—Curtis R. Davis
*Attorney, Agent, or Firm*—Carl G. Ries; Robert A. Kulason; Carl G. Seutter

[57] ABSTRACT

Charge hydrocarbon stream containing diisopropyl toluene isomers is catalytically treated to recover product stream containing increased proportions of 1-methyl-3,5-diisopropyl benzene.

5 Claims, 1 Drawing Figure

T - TOLUENE
C - CYMENES
P - PROPYLENE
DIPT - DIISOPROPYL TOLUENE
1M24 - 1-METHYL-2,4-DIISOPROPYL BENZENE
1M25 - 1-METHYL-2,5-DIISOPROPYL BENZENE
1M26 - 1-METHYL-2,6-DIISOPROPYL BENZENE
1M35 - 1-METHYL-3,5-DIISOPROPYL BENZENE
TIPT - TRIISOPROPYL TOLUENE

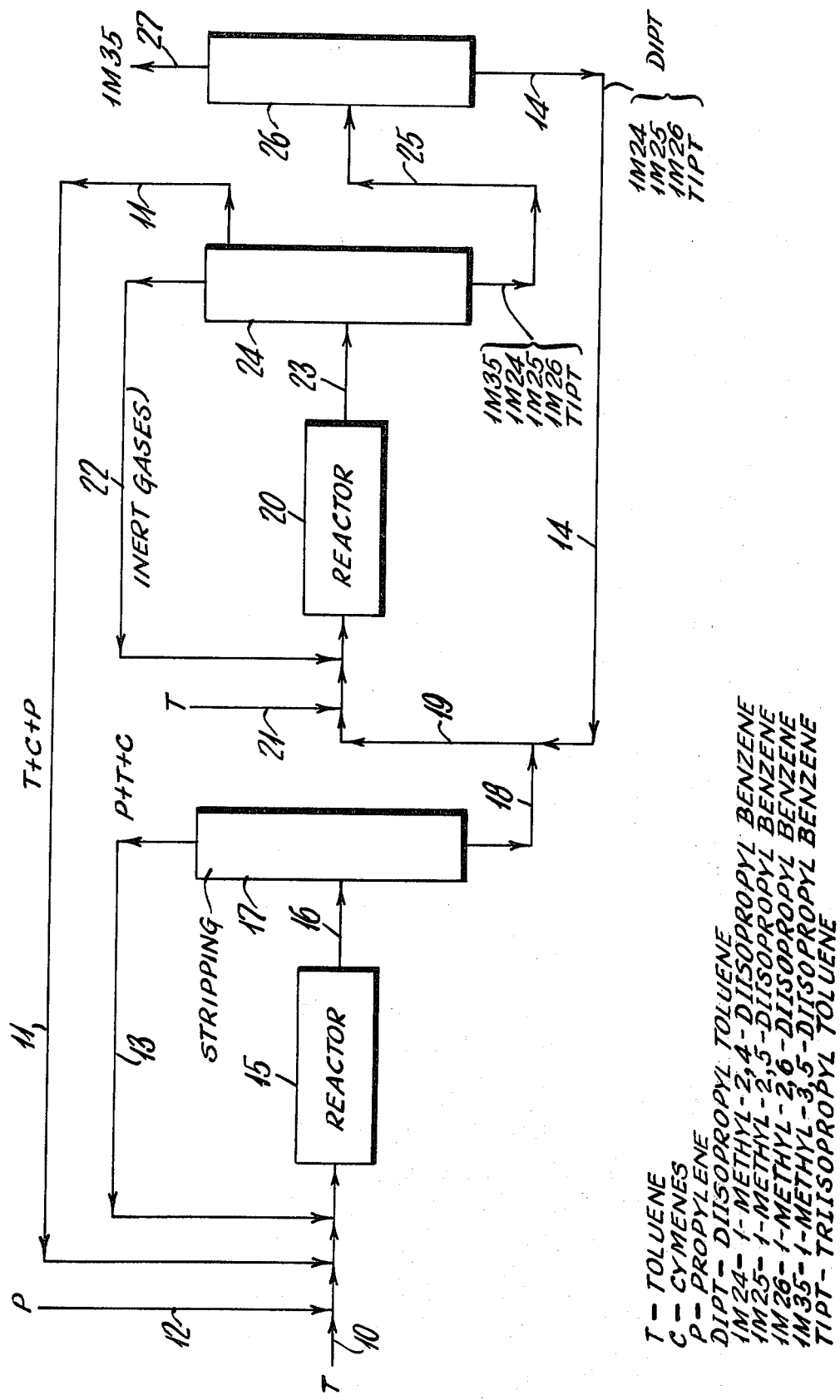

PREPARATION OF 1-METHYL-3,5-DIISOPROPYL BENZENE FROM CHARGE STREAMS CONTAINING DIISOPROPYL TOLUENE

FIELD OF THE INVENTION

This invention relates to the preparation of 1-methyl-3,5-diisopropyl benzene from charge streams containing diisopropyl toluene.

BACKGROUND OF THE INVENTION

Alkylaromatic hydrocarbons find wise use inter alia as raw materials for preparation of valuable chemical compounds. Alkylated toluene for example may be converted to desired products typified by symmetrical dihydroxy toluene (orcinol), trimesic acid (1,3,5-benzene tricarboxylic acid), etc. In particular, 1-methyl-3,5-diisopropyl benzene is a valuable chemical intermediate for the production of such products; but it is expensive to obtain in high purity.

When toluene or cymene is alkylated with propylene to prepare diisopropyl toluene, it is difficult to recover individual isomers from the product mixture. In a typical embodiment, it may be possible for example to separate by distillation a cut containing 71% 1-methyl-3,5-diisopropyl benzene and 29% 1-methyl-2,4-diisopropyl benzene from a charge containing 32% and 38% of these materials together with other isomers.

It is an object of this invention to provide a process for obtaining 1-methyl-3,5-diisopropyl benzene. Other objects will be apparent to those skilled in the art.

STATEMENT OF THE INVENTION

In accordance with certain of its aspects, the novel method of this invention may comprise
dealkylating in a dealkylation operation a charge stream containing desired 1-methyl-3,5-diisopropyl benzene and at least one other undesired diisopropyl toluene in the presence of dealkylating catalyst at dealkylating conditons including temperature of 200° F.–800° F. thereby forming dealkylated product stream containing 1-methyl-3,5-diisopropyl benzene and decreased proportions of said other undesired diisopropyl toluene in the diisopropyl toluene fraction;
recovering from said dealkylation operation said dealkylated product stream containing said 1-methyl-3,5-diisopropyl benzene and decreased proportions of other undesired diisopropyl toluenes in the diisopropyl toluene fraction; and
separating 1-methyl-3,5-diisopropyl benzene from said dealkylated product stream.

DESCRIPTION OF THE INVENTION

The charge stream which may be treated by the process of this invention contains at least one diisopropyl toluene. Although it may be possible to use as charge stream, a pure diisopropyl toluene such as pure 1-methyl-2,4-diisopropyl benzene (1M2,4), the advantages attainable by practice of the process of this invention may be achieved when the charge stream contains a mixture of isomers of diisopropyl toluenes. The charge stream may contain none of the desired 1-methyl-3,5-diisopropyl benzene (1M3,5) or it may contain substantial portions thereof, say 0%–75%; it will be found that the ratio of desired 1M3,5 isomer to undesired isomers may be desirably increased during processing. The typical charge may contain diisopropyl toluenes including the 1M3,5 isomer, the 1M2,4 isomer, the 1M2,5 isomer, and the 1M2,6 isomer. Under the conditions of operation the content of 1M3,5 isomer may be desirably increased.

It is a feature of the process of this invention that it may be readily employed in connection with a charge stream generated by the alkylation of toluene with propylene. Such a stream, after being stripped of propylene, may contain toluene, cymenes, and triisopropyl toluenes (TIPT) in addition to the four diisopropyl toluenes (DIPT) isomers noted above.

Alkylation of toluene to produce a charge stream which may be typical of those which may be treated by the process of this invention may be effected in a two-stage alkylation operation. In the first stage, propylene and toluene may be reacted in vapor phase at temperature of 300° F.–650° F., say 400° F. and 0–500 psig, say 500 psig and LHSV of 0.5–20 to form a substantially equilibrium mixture typically containing ca 5 w % o-cymene, 65 w % m-cymene, and 30 w % p-cymene. Preferred catalyst may be the Davison 979 brand of silica-alumina cracking catalyst containing 13% alumina and 87% silica.

The cymene product so obtained may then be alkylated in liquid phase with additional propylene at 100° F.–450° F. and 0–500 psig and LHSV of 0.5–20 in the presence of the same catalyst as is present in the vapor phase alkylation.

Product from alkylation commonly contains unreacted propylene, toluene, and cymene in addition to product diisopropyl toluenes and triisopropyl toluenes. The diisopropyl toluene (DIPT) present include the 1M3,5 isomer, the 1M2,4 isomer, the 1M2,5 isomer, and the 1M2,6 isomer.

One illustrative charge material obtained from two-step alkylation of toluene with propylene may contain, after materials lighter than diisopropyl toluenes have been stripped, 15.4 parts of 1M3,5 isomer, 37.2 parts of 1M2,4 isomer, 13.5 parts of 1M2,5 isomer, 1.6 parts of 1M2,6 isomer, and 17.2 parts of TIPT.

Charge material, to which there may be added a stream containing toluene, is passed to a reaction operation. During reaction, it is unexpectedly found that the 1M2,4 isomer, the 1M2,5 isomer, and the 1M2,6 isomer are isomerized to give increased proportions of the desired 1M3,5 isomer. Toluene and TIPT are transalkylated to yield increased proportions of DIPT and thus, because of isomerization, increased proportions of the desired 1M3,5 isomer. Dealkylation of the TIPT also increases the content of DIPT; and dealkylation of DIPT isomers (other than the 1M3,5 isomer) gives increasing proportions of cymenes. The 1M3,5 isomer charged to the reaction operation appears to pass through unchanged.

The net result of these operations is that the reactor effluent contains increased proportions of desired 1M3,5 isomer in the DIPT fraction. It also appears that a portion of the isomers, other than the 1M3,5 isomer, have been converted to the more readily separable cymenes. In one run, a charge containing no 1M3,5 isomer was converted to a product containing 59% of that isomer. In another run, a charge containing 29% 1M3,5 isomer was converted to a product containing 81% 1M3,5 DIPB.

Reaction is carried out in the presence of a selective dealkylation catalyst which selectively dealkylates DIPT isomers other than 1M3,5 DIPT. This catalyst also simultaneously dealkylates TIPT to DIPT. The catalyst simultaneously effects transalkylation (eg of TIPT and toluene to DIPT) and isomerization of undesired DIPT isomers to the desired 1M3,5 isomer.

Illustrative catalysts which may be employed include:
(i) silica-alumina typified by the Davison 979 brand of silica-alumina cracking catalyst containing 13% alumina and 87% silica;
(ii) zeolite catalysts typified by the rare-earth exchanged NaY zeolite;
(iii) silica-magnesia catalyst typified by a silica-magnesia cracking catalyst containing 70% silica and 30% magnesia;
(iv) halided alumina catalyst such as 0.47% Pt on eta-alumina which has been treated with carbon monoxide and sulfuryl fluoride at 700° F. for 4 hours to give product catalyst containing ca 3% fluorine; etc.

The conditions of reaction may vary depending on the particular catalyst. Generally temperature may be 200° F.–800° F., typically ca 350° F.–660° F., preferably 440° F.–550° F. say about 525° F. and slight vacuum to pressures up to as high as 500 psig, typically 0–200 psig, say 10 psig. When isomerization is the principal reaction desired, the temperatures may be typically 350° F.–550° F. When dealkylation (including transalkylation) is the principal reaction desired, the temperatures may be typically 450° F.–660° F. The latter may be the case when the charge contains substantial TIPT and there is added thereto toluene. Presence of an inert diluent gas, such as helium, is permissible. Space velocities of the order of 0.5–10 parts of charge per hour per part of catalyst are effective.

It is an advantageous feature of the process of this invention that although it may permit attainment of product stream containing increased proportions of 1M3,5 isomer from a charge stream containing this isomer together with other DIPT isomers, it also may be used to treat other streams. For example, it is possible to treat charge streams (containing none of the 1M3,5 isomer) which contain only other DIPT isomers either pure or in the admixture. For example, it is possible to treat a charge stream containing pure 1M2,4 isomer or pure 1M2,5 isomer.

It is unexpected to find that the undesired DIPT isomers, viz the 1M2,4 isomer and the 1M2,5 isomer and the 1M2,6 isomer are selectively dealkylated to the corresponding cymenes and that the desired 1M3,5 isomer appears not to be destroyed during that selective dealkylation. It is also unexpected to find that simultaneously the undesired DIPT isomers may isomerize to produce increased amounts of the desired 1M3,5 isomer.

Product stream from selective dealkylation-isomerization is recovered and passed to a separation operation from which these are recovered inert gases, toluene, and cymenes leaving a stream containing DIPT isomers and TIPT isomers. This stream is preferably further distilled to recover, as overhead 1M3,5 isomer and, as bottoms, the other DIPT isomers plus the TIPT isomers.

DESCRIPTION OF SPECIFIC EMBODIMENTS

Practice of the process of this invention will be apparent to those skilled in the art from the following wherein, as elsewhere in this description, all parts and percents are by weight unless otherwise specified.

EXAMPLES 1–3

In this series of Examples, 2.3 ml. per hour of Feed Stream A containing inter alia toluene and tri-isopropyl toluene may be subjected to transalkylation in the presence of flowing helium (50 cc/min) and Davison 979 FCC silica-alumina 20–80 mesh catalyst, at 525° F.–605° F. and 165–480 psig to effect transalkylation giving a product stream in which the concentration of desired 1M3,5 isomer is increased from its initial 15.4% up to as high as 35.4%. Simultaneously, the concentration of the undesired 1M2,4 isomer is decreased from its initial 37.2% down to as low as 9.8%.

EXAMPLES 4–5

In this series of Examples, 2.3 ml per hour of Feed Stream B containing substantial proportions of triisopropyl toluene (TIPT) may be subjected to dealkylation in the presence of flowing helium (50 cc/min) and Davison 979 FCC silica-alumina 20–80 mesh catalyst (1 g) at 495°–513° F. and atmospheric pressure to effect dealkylation of TIPT, the concentration thereof decreasing from 46.9% to 0.6–0.7% as the concentration of desired 1M3,5 isomer increases from 4.2% to a product stream level of 15.1–19.4%.

EXAMPLES 6–10

In this series of Examples, 2.3 ml per hour of Feed stream C containing 29.3% of desired 1M3,5 isomer and 69.0% of undesired 1M2,4 isomer is subjected to isomerization-dealkylation in the presence of flowing helium (50 cc/min) and Davison 979 FCC silica-alumina 20–80 mesh catalyst (1 g) at 447°–656° F. and atmospheric pressure to effect isomerization. The concentration of desired 1M3,5 isomer is increased to as high as 36.9%; and the concentration of undesired 1M2,4 isomer is decreased to 33.5%.

EXAMPLES 11–15

In this series of Examples, Feed Stream D containing 88.5% of undesired 1M2,5 isomers and 0% of desired 1M3,5 isomer is subjected to isomerization-dealkylation in the presence of flowing helium (50 cc/min) and Davison 979 FCC silica-alumin 20–80 mesh catalyst (1 g) at 368°–391° F. at atmospheric pressure to effect isomerization. The concentration of undesired 1M2,5 isomer is decreased from 88.5% to as low as 15.1%; and the concentration of desired 1M3,5 isomer is increased from 0% to as high as 45.5%.

EXAMPLE 16

In this Example, it is shown that it is possible to upgrade a charge stream containing a relatively high content of desired 1M3,5 isomer. Feed Stream E containing 70.7% of desired 1M3,5 and 29.3% of undesired 1M2,4 (a ratio of desired to undesired of 2.42) is isomerized at 515° F. at atmospheric pressure and conditions otherwise comparable to those of Examples 11–15. Product stream contains 68.1% of desired isomer and the ratio of desired isomer to undesired isomer has desirably increased to 5.05—more than doubled.

In the following table there are set forth the temperature (°F.), pressure (psig), weight hourly space velocity (WHSV), and, for Examples 1–15, the rate of Flow of helium (cc/minute). Composition (in weight percent) is shown for the various streams.

| Example | Temp. | Press. | WHSV | He | Toluene | Cymenes | DIPT 1M35 | 1M24 | 1M25 | 1M26 | TIPT |
| --- | --- | --- | --- | --- | --- | --- | --- | --- | --- | --- | --- |
| Feed A | — | — | — | — | 14.9 | 0.1 | 15.4 | 37.2 | 13.5 | 1.6 | 17.2 |
| 1 | 525 | 165 | 1.6 | 50 | 5.1 | 34.5 | 35.4 | 13.7 | 9.5 | 0.3 | 1.4 |
| 2 | 530 | 360 | 1.6 | 50 | 6.0 | 32.9 | 27.2 | 20.0 | 11.0 | 0.5 | 2.3 |
| 3 | 605 | 480 | 1.6 | 50 | 7.2 | 46.5 | 29.3 | 9.8 | 6.3 | 0.4 | 0.2 |
| Feed B | — | — | — | — | — | 2.2 | 4.2 | 22.5 | 23.7 | 0.7 | 46.9 |
| 4 | 494 | 0 | 2.4 | 50 | 0.13 | 34.7 | 19.4 | 29.0 | 15.9 | 0.1 | 0.7 |
| 5 | 513 | 0 | 2.4 | 50 | 0.17 | 29.9 | 15.1 | 35.0 | 18.9 | 0.7 | 0.6 |
| Feed C | — | — | — | — | 0 | 0 | 29.3 | 69.0 | 1.6 | 0 | 0 |
| 6 | 447 | 0 | 2.6 | 50 | 0.1 | 22.2 | 36.9 | 33.5 | 6.3 | 0.1 | 1.0 |
| 7 | 479 | 0 | 2.6 | 50 | 0.1 | 26.8 | 37.1 | 29.4 | 5.6 | 0.1 | 0.8 |
| 8 | 550 | 0 | 2.6 | 50 | 0.4 | 38.2 | 35.3 | 22.6 | 3.4 | 0.1 | 0.3 |
| 9 | 600 | 0 | 2.6 | 50 | 1.3 | 51.9 | 31.9 | 13.0 | 1.8 | 0.1 | 0 |
| 10 | 656 | 0 | 2.6 | 50 | 3.0 | 61.9 | 28.0 | 5.6 | 1.0 | 0.05 | 0 |
| Feed D | — | — | — | — | 0 | 0 | 0 | 5.3 | 88.5 | 6.5 | 0 |
| 11 | 368 | 0 | 1.3 | 10 | 0.2 | 17.8 | 45.5 | 16.4 | 15.1 | 0.2 | 2.7 |
| 12 | 371 | 0 | 2.6 | 9.6 | 0.2 | 11.4 | 14.6 | 13.9 | 54.6 | 0.3 | 4.9 |
| 13 | 392 | 0 | 1.3 | 6.9 | 0.2 | 20.3 | 39.1 | 17.4 | 18.5 | 0.2 | 2.1 |
| 14 | 395 | 0 | 2.6 | 7.5 | 0.2 | 16.4 | 19.7 | 16.4 | 42.7 | 0.2 | 4.3 |
| 15 | 391 | 0 | 1.3 | 0 | 0.1 | 9.9 | 28.9 | 17.2 | 33.4 | 0.2 | 9.1 |
| Feed E | — | — | — | — | 0 | 0 | 70.7 | 29.3 | 0.3 | 0 | 0 |
| 16 | 515 | 0 | 2.3 | — | 0.2 | 16.3 | 68.1 | 13.4 | 1.8 | 0 | 0.3 |

EXAMPLE 17

There is set forth in the drawing a schematic flow sheet indicating a preferred embodiment of the method of carrying out the process of this invention. This drawing is schematic and does not show details of various operations including pumps, heat exchangers, etc.

Fresh charge toluene is admitted through line 10 together with recycle stream in line 11 which contains propylene, toluene, and cymenes. Fresh propylene is admitted through line 12.

Reaction operation 15 may include two stages, not separately shown, each containing Davison 979 brand silica-alumina cracking catalyst. In the first stage the above-noted composition (71.5 mole % toluene and 28.1 mole % propylene) is subjected to alkylation in vapor phase at 505° F. and 500 psig to yield product containing 38 w % cymenes (32 w % p-cymene, 64 w % m-cymene, and 4 w o-cymene). This mixture is fractionated (not shown) to recover a bottom cut of cymenes and heavier for further alkylation in a second stage with propylene, mole ratio of cymene:propylene of about 1:1. (The toluene is recycled to the first step). Further alkylation is effected in liquid phase at 200° F. and 250 psig. Product stream in line 16 contains principally diisopropyl toluene and triisopropyl toluene. Content of diisopropyl toluenes may be 35 w %.

Unreacted propylene is stripped in stripping operation 17, the propylene being recovered in line 13 and preferably recycled to reaction 15. Stripped bottoms, recovered in line 18 contain diisopropyl toluenes and triisopropyl toluenes.

Stripped bottoms in line 18 are passed through line 19 to reactor 20. There may optionally be added, recycle material from line 14. Preferably inert gas is added via line 22. In reaction operation 20, catalytic isomerization-dealkylation (together with transalkylation because of toluene admitted through line 21) is effected at 0 psig and 550° F. in the presence of silica-alumina cracking catalyst.

It should be noted that the system may be controlled so that reactor 20 is operated primarily as an isomerization operation (isomerization mode) or alternatively as a dealkylation (including transalkylation) isomerization operation (dealkylation mode). The former mode is useful when the stream in line 19 admitted to the reactor 20 contains smaller amounts of triisopropyl toluene. When the amount of triisopropyl toluene is higher, then it may be desirable to run reactor 20 so that dealkylation (including transalkylation) is effected therein. In the latter dealkylation (including transalkylation) mode, toluene is admitted through line 21; in the isomerization mode, it may not be necessary to add toluene through line 21. The reaction conditions (temperature, pressure, catalyst, etc.) may be generally similar in either the isomerization mode or in the transalkylation mode.

During reaction operation 20, the triisopropyl toluenes are dealkylated. At least some of the 1M2,4 and the 1M2,5 and 1M2,6 are converted to the desired 1M3,5 isomer by isomerization. Simultaneously, at least a portion of the 1M2,4, and the 1M2,5 and 1M2,6 is dealkylated to the corresponding cymenes. Toluene and TIPT are transalkylated to yield increased proportions of DIPT and thus (because of the simultaneous isomerization and dealkylation) increased proportions of 1M3,5. The 1M3,5 isomer passes through reaction operation 20 substantially untouched.

The net result of reaction operation 20 is to produce in line 23 a product stream which is enriched with respect to desired 1M3,5 isomer in the DIPT fraction. This stream in line 23 also contains toluene, cymenes, and TIPT in addition to inert gas.

The stream in line 23 is passed to separation operation 24, schematically shown, from which is recovered through line 11 a stream containing toluene, cymenes, and propylene which may be recycled to reaction operation 15 and a stream of inert gas (helium) which may be recycled through line 22 to reaction operation 20.

Bottoms from separation operation 24 contain TIPT, 1M2,4 isomer; 1M2,5 isomer; 1M2,6 isomer, plus increased proportions of 1M3,5 isomer. The stream in line 25 is distilled in distillation operation 26 to give, as overhead in line 27, desired 1M3,5 isomer. Bottoms, recovered in line 14 contain TIPT plus the diisopropyl toluenes 1M2,4 and 1M2,5 and 1M2,6. This latter stream may be recycled through lines 14 and 19.

Although this invention has been illustrated by reference to specific embodiments, it will be apparent to those skilled in the art that various changes and modifications may be made which clearly fall within the scope of this invention.

We claim:

1. The method which comprises dealkylating in a dealkylation operation a charge stream containing desired 1-methyl-3,5-diisopropyl benzene and at least one other undesired diisopropyl toluene in the presence of dealkylating catalyst at dealkylating conditions including temperature of 200° F.–800° F. thereby forming dealkylated product stream containing 1-methyl-3,5-diisopropyl benzene and decreased proportions of said other undesired diisopropyl toluene in the diisopropyl toluene fraction;

recovering from said dealkylation operation said dealkylated product stream containing said 1-methyl-3,5-diisopropyl benzene and decreased proportions of other undesired diisopropyl toluenes in the diisopropyl toluene fraction; and separating 1-methyl-3,5-diisopropyl benzene from said dealkylated product stream.

2. The method claimed in claim 1 wherein said charge stream contains triisopropyl toluenes which are dealkylated to diisopropyl toluenes.

3. The method claimed in claim 1 wherein said dealkylating conditions include temperature of about 350° F.–660° F.

4. The method claimed in claim 1 wherein said dealkylating conditions include temperature of about 450° F.–660° F.

5. The method claimed in claim 1 wherein said dealkylating catalyst contains silica-alumina.

* * * * *